(12) United States Patent
Schilling

(10) Patent No.: US 7,755,055 B2
(45) Date of Patent: Jul. 13, 2010

(54) DATA TRANSMISSION SYSTEM FOR COMPUTER TOMOGRAPHS

(75) Inventor: Harry Schilling, Eichstaett (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 238 days.

(21) Appl. No.: 11/422,275

(22) Filed: Jun. 5, 2006

(65) Prior Publication Data

US 2006/0274853 A1    Dec. 7, 2006

(30) Foreign Application Priority Data

Jun. 6, 2005   (DE) ...................... 10 2005 026 158

(51) Int. Cl.
*H04L 27/00*   (2006.01)
(52) U.S. Cl. ................................. 250/370.09
(58) Field of Classification Search ............ 250/363.04; 378/4; 375/295, 316, 358
See application file for complete search history.

(56) References Cited

U.S. PATENT DOCUMENTS

| | | | | | |
|---|---|---|---|---|---|
| 4,928,283 | A | * | 5/1990 | Gordon ...................... | 378/20 |
| 5,204,979 | A | * | 4/1993 | Schenkyr et al. ......... | 455/276.1 |
| 5,416,815 | A | * | 5/1995 | Hsieh ............................ | 378/4 |
| 5,577,026 | A | * | 11/1996 | Gordon et al. .............. | 370/278 |
| 6,085,076 | A | * | 7/2000 | Lindsay et al. ............ | 455/277.1 |
| 6,426,992 | B1 | * | 7/2002 | Kohler et al. ................. | 378/19 |
| 6,433,631 | B2 | * | 8/2002 | Pearson et al. .............. | 329/311 |
| 6,470,047 | B1 | * | 10/2002 | Kleinerman et al. ........ | 375/232 |
| 7,079,619 | B2 | * | 7/2006 | Katcha et al. ................ | 378/15 |
| 7,248,641 | B2 | * | 7/2007 | Schilling et al. ............ | 375/295 |
| 2002/0061051 | A1 | * | 5/2002 | Kitahara ...................... | 375/144 |
| 2003/0092379 | A1 | * | 5/2003 | Brothers et al. ............ | 455/12.1 |
| 2003/0142023 | A1 | * | 7/2003 | Djuknic ....................... | 343/703 |
| 2003/0153322 | A1 | * | 8/2003 | Burke et al. ................. | 455/450 |
| 2003/0162566 | A1 | * | 8/2003 | Shapira et al. .............. | 455/561 |
| 2003/0185310 | A1 | * | 10/2003 | Ketchum et al. ............ | 375/259 |
| 2003/0228857 | A1 | * | 12/2003 | Maeki ...................... | 455/278.1 |
| 2006/0009168 | A1 | * | 1/2006 | Khan et al. .................. | 455/101 |
| 2006/0034381 | A1 | * | 2/2006 | Ionescu et al. .............. | 375/267 |
| 2006/0202894 | A1 | * | 9/2006 | Nassimi ............... | 343/700 MS |

FOREIGN PATENT DOCUMENTS

| | | |
|---|---|---|
| DE | 4006007 | 8/1990 |
| DE | 4218692 | 3/1993 |

* cited by examiner

*Primary Examiner*—David P Porta
*Assistant Examiner*—Djura Malevic
(74) *Attorney, Agent, or Firm*—Kevin L. Daffer; Daffer McDaniel, LLP

(57) ABSTRACT

A computer tomograph comprises a rotating part and a stationary part, and includes a system for transmitting data between the rotating part and the stationary part with a directional radio link. The system comprises an antenna arrangement for directional emission of data signals from the rotating part along a direction of a rotation axis of the rotating part, and for directionally sensitive reception of data signals at a patient's table on the stationary part.

29 Claims, 1 Drawing Sheet

DATA TRANSMISSION SYSTEM FOR COMPUTER TOMOGRAPHS

PRIORITY CLAIM

This application claims priority to German Application No. 10 2005 026 158.2 filed Jun. 6, 2005.

BACKGROUND OF THE INVENTION

1. Field of the Invention

The invention relates to a data transmission system for transmitting data between a rotating part and a stationary part of a computer tomograph by means of directed radio transmission.

2. Description of the Prior Art

A device for data transmission in computer tomographs is known from U.S. Pat. No. 6,433,631. A transmitter signal is made to impinge on a strip conductor line in a rotating part. A tap provided on a stationary part is kept at a small distance of an order of magnitude of about 1 mm from the strip conductor line.

Usually the transmission systems known from prior art can be incorporated in computer tomographs or their rotary joints only at large expenditure of means. Thus, they may be assembled to form independent units, but for this they need a support along the circumference of the device, which involves high outlay. When incorporated into existing sliprings, these transmission systems are easily subject to interference from adjacent energy transmission tracks.

BRIEF SUMMARY OF THE INVENTION

It is the object of the invention to provide a computer tomograph having a data transmission system that is substantially non-sensitive to mechanical tolerances and can be incorporated in a computer tomograph with small mechanical outlay.

In accordance with the invention, this object is achieved with a computer tomograph comprising a rotating part and a stationary part, with a system for transmission of data between the rotating part and the stationary part, in which the rotating part comprises: at least one data source such as an X-ray detector; at least one first transmitter means for receiving data from the data source and converting received data to data signals for transmission to the stationary part; and one first transmitter antenna arrangement for transmitting the data signals; wherein the stationary part comprises: a first receiver antenna arrangement for picking-up data signals transmitted by the first transmitter antenna arrangement; at least one first receiver means for receiving data signals from the first receiver antenna arrangement and converting the received data signals for relay of data to a data sink; at least one data sink for evaluating data relayed from the receiver means; and a patient's table adapted to move along a direction of an axis of the rotating part.

BRIEF DESCRIPTION OF THE DRAWINGS

In the following the invention will be described on examples of embodiment without limitation of the general inventive concept, and with reference to the drawings.

DETAILED DESCRIPTION OF PREFERRED EMBODIMENTS

Figure 1:
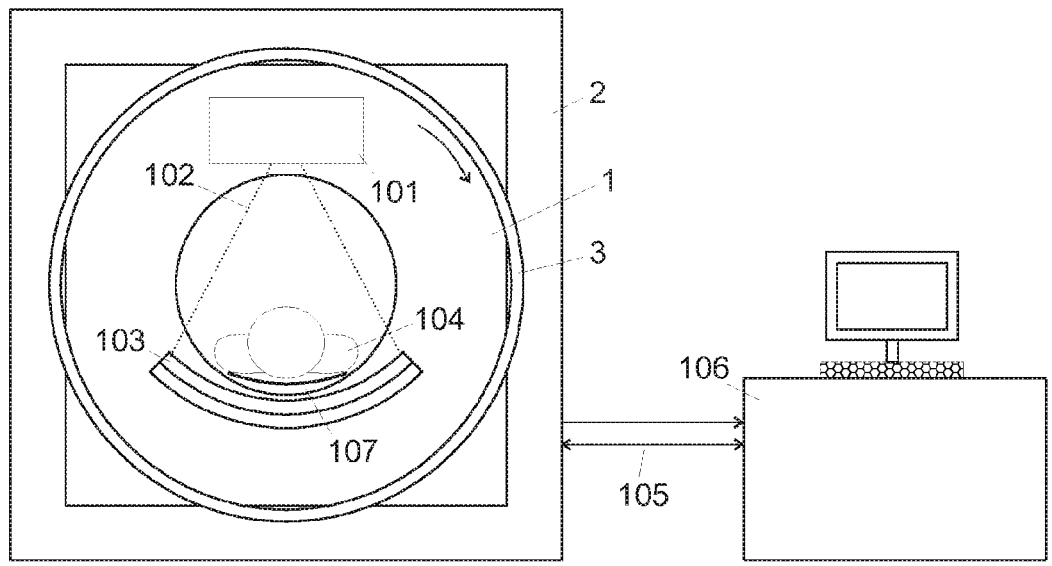
FIG. 1 schematically shows a computer tomograph in a general form.

A computer tomograph in accordance with the invention, having a system for transmitting data between a rotating part and a stationary part, comprises at least one data source on the rotating part, and at least one data sink on the stationary part. A data source may be, for example, an X-ray detector or its DAS (data acquisition system), or also any other control means or computers. A data sink may be a computer for evaluating and processing the data, but also another control unit.

Furthermore, at least one first transmitter means and also a transmitter antenna arrangement fed thereby are provided in the rotating part. A first transmitter means of this kind receives data from the data source and converts them for emission by the transmitter antenna arrangement. Moreover, at least one first receiver means is provided in the stationary part to be fed by a receiver antenna arrangement. The receiver means converts the signals received from the receiver antenna arrangement for relay to the data sink.

The signals may be modulated by the transmitter means according to prior art. However, it is of especial advantage for these signals to be exclusively encoded. By a suitable encoding with long word length, the signals may be also transmitted in a base band, when their lower limiting frequency is higher than the lower limiting frequency of the arrangement.

An especially advantageous embodiment of the invention provides at least one second transmitter means in the stationary part, and at least one second receiver means in the rotating part. With this embodiment, a communication from the stationary part to the rotating part is also possible. With most computer tomographs the data rate in this direction is lower than that from the rotating part to the stationary part, because here only few control data need be transmitted instead of image data.

Furthermore, optionally at least one second transmitter antenna arrangement, fed by a second transmitter means, is provided in the stationary part. In addition, at least one second transmitter arrangement is provided in the rotating part for feeding a second receiver arrangement. With this, separate antennas are provided also for the direction of the rotating part to the stationary part.

Alternatively, the antennas may also be used in common for both directions. For this, however, provision need be made for a decoupling between the directions of transmission by suitable measures such as a selection of frequency or a selection of direction.

It is of special advantage to use a different transmission system for transmission from the stationary to the rotating part, and thus, for example, a simplified antenna arrangement with omni-directional characteristics, or a modulation with large bandwidth but lower data rate, could be used to advantage. With the large bandwidth, preferably accompanied by lower transmission power, good transmission characteristics together with good EMC properties may nevertheless be achieved. Of special advantage would be a spread spectrum modulation, such as DSSI for example.

In another advantageous embodiment of the invention, optionally the transmitter antenna arrangement, but most preferably the receiver antenna arrangement, is designed to be a diversity antenna system. In a case of reception, for example, a diversity antenna system of this kind selects the most suitable antenna from a plurality of antennas. The signal strength (electrical field strength), or also the signal/noise ratio, may be used, for example, as selection parameters.

An advantageous embodiment of a diversity system consists in the selection of the antennas being effected according to the relative position of the rotating part to the stationary part. Thus, for example, details concerning the best antenna for each case may be stored in a memory and retrieved in dependence upon position. Furthermore, an optimum configuration could be adaptively learned by means of measurements performed in an interval condition.

In another embodiment of the invention, optionally the transmitter antenna arrangement and/or the receiver antenna arrangement are designed to be a phased array. A phased array of this kind comprises a plurality of radiators supplied with signals having a defined relationship to each other, so that a definite radiation pattern may be obtained in its entirety. A phased array of this kind may be operated with fixed set phase relationships between the individual radiators, or also with variable phase relationships.

Another advantageous embodiment of an arrangement with a phased array consists in the patterns for the individual antennas being obtained in dependence upon the relative position of the rotating part to the stationary part. Thus, for example, it is possible to retrieve position-dependent preprogrammed radiation patterns. Here too, a learning device which, for example, measures the transmission conditions during transmission intervals and stores them for later transmission tasks, is feasible.

In a specially advantageous embodiment, a control unit is provided for setting or choosing the patterns of individual antennas according to predetermined parameters, or selecting particular antennas from an arrangement having a plurality of antennas. The predetermined parameters for setting or choosing or selecting are, for example, the signal level, the signal-to-noise ratio, the bit error rate, the transit time, and/or the phase shift based on a reference signal. All of these parameters are a measure of a certain aspect of transmission quality. Of course, other parameters or combinations of parameters may be chosen.

In an especially advantageous embodiment of the invention, a first receiver antenna arrangement and/or a second transmitter antenna arrangement are incorporated at least optionally in a patient's table. The incorporation may be effected, for example, in a side of a stand of the patient's table facing the rotating part. For this, it is particularly expedient for an antenna arrangement to be disposed as close as possible to the rotation axis of the rotating part. In the following, the term "antenna arrangement" refers optionally to a transmitter antenna arrangement and/or a receiver antenna arrangement.

It is of special advantage for an antenna arrangement to be incorporated in the berth of the patient's table. This enables it to be mounted as close as possible to the rotation axis of the rotating part. Thereby an antenna arrangement can be placed also into a plane of rotation of the rotating part. Furthermore, an attenuation by a patient's body has an advantageous effect of suppressing reflections of the signals. Another improvement is obtained when the patient's table is made of an electrically absorbing material, or is surrounded by absorber material. Of course, parts of the computer tomograph also may be coated or filled with absorber material.

Especially with an arrangement within the patient's table, it is of advantage to achieve an antenna arrangement with non-metallic materials. Thus the radiation field of X-ray radiation will be affected as little as possible.

Here it is of advantage to achieve at least one antenna arrangement with non-metallic, electrically conducting materials, such as those based on carbon, for example.

It is especially advantageous to use dielectric waveguides for the antenna arrangement. These may be built up entirely without metal, using plastic materials which hardly affect the radiation field. Similarly, a conducting of signals to the antenna arrangement may be effected by means of dielectric waveguides.

In another advantageous embodiment, the radiation pattern of at least one antenna arrangement is controlled. In order to achieve a transmission which is as free of interference as possible, at least one antenna arrangement within the patient's table can be controlled to have an antenna pattern with a major lobe directed towards the rotating part, and preferably lying in a plane perpendicular to the rotation axis of the rotating part. Outside interference sources can be well suppressed with a radiation pattern of this kind. In particular, reflections of sent signals at parts of the computer tomograph also may be suppressed. If these reflections were to be superimposed upon a wanted signal upon being received, then this could lead to considerable interference with reception. If, for example, a signal having a data rate of 1 Gbit/s is transmitted, then the free space length of one bit is about 30 cm. Thus a superposition of only one wave delayed by a detour of only 30 cm on a directly received wave would already lead to a superposition of one bit on the preceding bit.

In another embodiment of the invention, at least one antenna arrangement in the patient's table is driven so that the major lobe of the radiation pattern is directed onto a plane of the rotating part, irrespective of shifts of the patient's table along a longitudinal direction. With this, focusing onto a particular plane or onto a particular position of the rotating part can be achieved with a tracking movement of the antenna pattern, without dependence upon an exact positioning of the patient's table.

Another embodiment of the invention provides for at least one antenna arrangement in the patient's table to comprise a plurality of elements which extend along a direction transverse to the patient's table and which are disposed along the longitudinal direction of the patient's table. By means of a control unit these now may be optionally selected, and/or driven with phases shifted with respect to each other, according to the position of the patient's table. Thus, the radiation pattern may be shifted along planes perpendicular to the longitudinal axis of the patient's table.

Another embodiment of the invention provides for the radiation pattern of at least one antenna arrangement in the patient's table to be controlled in accordance with the rotational movement between the rotating part and the stationary part. Thereby the radiation pattern may follow the rotational movement. This makes it possible for the radiation pattern to be more strongly bundled in the form of a lobe, instead of that of a toroid.

Furthermore, at least one antenna arrangement on the rotating part may have an antenna pattern with a major lobe directed onto the patient's table. Here it is particularly expedient to design the antenna along the direction of the axis of the computer tomograph, and to be curved around the axis of the computer tomograph and an additional extension, because hereby a radiation pattern focused on one point or a line of the rotation axis can be achieved.

Furthermore, it is of advantage for at least one antenna arrangement on the rotating part to consist of a plurality of partial radiators. These may now be driven in dependence upon the angular position of the rotating part so that preferably one major lobe of a partial radiator is directed exactly onto a predetermined axis, preferably parallel to the rotation axis of the computer tomograph. Here control may be achieved by selection of a suitable partial radiator, and/or also by phase-controlled driving of a plurality of partial radiators.

Furthermore, it is of advantage for at least one antenna arrangement on the rotating part to consist of a plurality of partial radiators. These may now be driven in dependence upon the angular position of the rotating part so that preferably exactly one major lobe of a partial radiator is directed onto a predetermined position on the patient's table, preferably onto its underside. Control can here be achieved by selection of a suitable partial radiator, and/or also by phase-controlled driving of a plurality of partial radiators.

Another advantageous embodiment of the invention comprises a plurality of antennas of an antenna arrangement, which are in-phase fed and/or adapted for in-phase feeding of a receiver unit, with reference to a modulation signal. A preferable focusing onto the longitudinal axis of a patient's table extending approximately parallel to the rotation axis of the rotating part, but more preferably onto the rotation axis of the rotating part, results in constant signal transit times to this axis from any point with constant radius. Therefore no phase shift of the signal results during a change of antenna segments owing to the rotation. If individual antenna segments are mounted on the rotating part at different distances from a receiver antenna which may be incorporated in the patient's table, for example, then the path difference can be compensated by a suitable shortening or lengthening of leads to respective antenna segments.

Another advantageous embodiment of the invention consists of an additional control unit being provided for controlling bidirectional communication. This control unit sets time frames for each direction of communication. These are preferably apportioned according to the prevailing data volume. If for example, a data rate of 1 Gbit/s is required from the rotating part 1 to the stationary part 2, and a data rate of only 10 Mbits/s is required in the opposite direction, then preferably the ratio of the time frames is about 100:1.

For communication, a computer tomograph in accordance with the invention comprises at least one of the devices described here.

In the present document reference is being made to a transmission from the rotating part to the stationary part of a computer tomograph, in order to simplify the illustration. Of course, a device in accordance with the invention may also be used for the opposite direction of transmission. Similarly, a device in accordance with the invention may also be used in other applications of rotating data transmission, and similarly also for linear transmission between two units that are movable relative to each other.

A direction of transmission from a rotor to a stator is described here, because it corresponds to the most frequent case of use. However, transmission in the opposite direction, or also bidirectional transmission, is similarly possible.

In accordance with conventional terminology in the field of antenna technology, the term "antenna" or "radiator" is being used for both transmitter antennas and receiver antennas, because antennas are always reciprocal building components.

FIG. 1 shows an example of a device in accordance with the invention. A computer tomograph (CT scanner) consists of two main mechanical components. A stationary part 2 serves as a base and frame of the entire instrument in which a rotating part 1 revolves. A patient 104 is positioned on a berth 107 within an opening of the rotating part. An X-ray tube 101 and an oppositely disposed detector 103 are provided for scanning the patient by means of X-rays. The X-ray tube 101 and the detector 103 are disposed to be rotatable on the rotating part 1. A rotary joint 3 serves as an electrical link between the rotating part 1 and the stationary part 2. By means of this, high electric power for feeding the X-ray tube 101 is transmitted in the direction of the rotating part 1, and at the same time raw image data are transmitted in the opposite direction. Communication of control data in both directions is provided in parallel with this. An evaluation and control unit 106 serves for operating the computer tomograph, and also for displaying generated images. Communication with the computer tomograph is effected via a bidirectional link 105.

Figure 2:
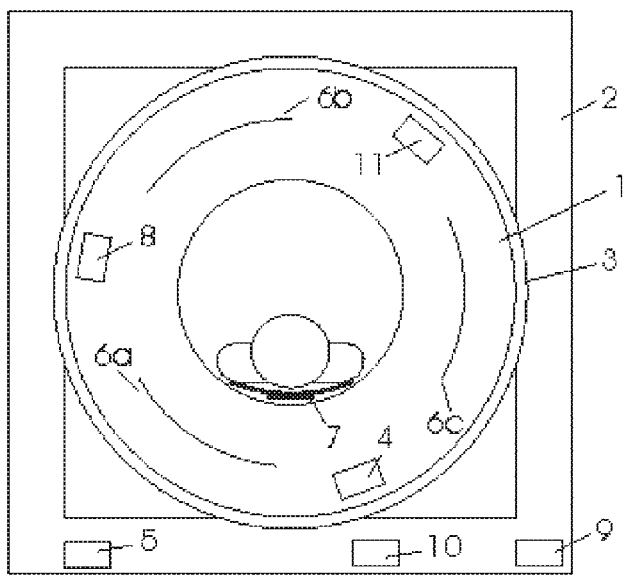
FIG. 2 schematically shows an arrangement of transmitter/receiver means and antennas.

FIG. 2 shows in a simplified form an example of an arrangement of a computer tomograph in accordance with the invention, together with antennas needed for transmitting, and other components. Data from a data source 4 (detector 103 with subsequent signal processing or DAS) on the rotating part 1 are processed by means of a first transmitter means 8 and relayed to a transmitter antenna arrangement, here depicted as consisting of three parts 6a, 6b, 6c. Now this transmitter antenna arrangement radiates high frequency signals in a direction of the receiver antenna arrangement 7. As an example, a receiver antenna arrangement has been shown below a patient's berth 107 on the stationary part 2. The signals picked up from this receiver antenna arrangement 7 are relayed for processing to a first receiver means 9. Output signals from this are then conducted to a data sink 5. For the case of communication occurring in the opposite direction, i.e. from the stationary part to the rotating part, a second transmitter means 10 is provided on the stationary part 2, and a second receiver means 11 on the rotating part 1. In this example, a link between a transmitter means and receiver means is effected via the receiver antenna arrangement 7 and the transmitter antenna arrangement 6, although in an opposite direction. For this, suitable means for selecting the directions should be provided, for example directional selection with light couplers, polarization selection, or also frequency selection. Similarly, certain time frames could be preset for communication in each direction. These could then also be adapted to different amounts of data.

Parts of the transmitter antenna arrangement 6a, 6b, 6c are here depicted by way of an example of embodiment as being curved to achieve a focus on an axis parallel to the rotation axis of the computer tomograph. With an additional extension of the arrangement along the direction of the rotation axis, the length of the focus may even be limited to a point. As the position of the receiver antenna arrangement 7 is usually only close to, but not on the rotation axis of the computer tomograph, the radiation patterns of the components of the transmitter antenna arrangement could be made to perform tracking mechanically or electronically in dependence upon position. In most cases, however, any deviation should be tolerable.

The invention claimed is:

1. A computer tomograph comprising a rotating part and a stationary part, with a system for transmission of data between the rotating part and the stationary part, in which the rotating part comprises:
    at least one data source;
    at least one first transmitter means for receiving data from the data source and converting received data to data signals for transmission to the stationary part; and
    a first transmitter antenna arrangement for transmitting the data signals;
wherein the stationary part comprises:
    a first receiver antenna arrangement for picking-up data signals transmitted by the first transmitter antenna arrangement;
    at least one first receiver means for receiving data signals from the first receiver antenna arrangement and converting the received data signals for relay of data to a data sink;
    at least one data sink for evaluating data relayed from the receiver means; and
    a patient's table adapted to move along a direction of an axis of the rotating part;
wherein at least one of the first transmitter antenna arrangement and the first receiver antenna arrangement is a diversity antenna system;
wherein the system for transmission of data comprises a control unit configured to selectively employ a phased array antenna system, which comprises a plurality of radiators of the first transmitter antenna arrangement for transmitting in phase relationship with each other, so that a definite radiation pattern may be obtained in its entirety; and wherein patterns for the individual antennas are obtained in dependence upon the relative position of the rotating part to the stationary part by retrieving position dependent preprogrammed radiation patterns.

2. The computer tomograph according to claim 1, wherein the stationary part further comprises at least one second transmitter means, and the rotating part comprises at least one second receiver means.

3. The computer tomograph according to claim 2, wherein the stationary part further comprises at least one second transmitter antenna arrangement fed by the second transmitter means, and the rotating part further comprises one second receiver antenna arrangement for feeding the second receiver means.

4. The computer tomograph according to claim 1, wherein the first receiver antenna arrangement in the stationary part is fed by a second transmitter means with signals for emission.

5. The computer tomograph according to claim 1, wherein the first transmitter antenna arrangement in the rotating part is adapted to feed a second receiver means.

6. The computer tomograph according to claim 1, wherein the control unit is further configured to control patterns of individual antennas of the phased array antenna system according to relative positions of the rotating part to the stationary part.

7. The computer tomograph according to claim 1, wherein the control unit is configured to selectively employ an antenna of the diversity antenna system according to at least one transmission parameter selected from the group consisting of: signal level, signal-to-noise ratio, bit error rate, signal transit time, and signal phase shift referred to a reference signal.

8. The computer tomograph according to claim 3, wherein at least one of the first receiver antenna arrangement and the second transmitter antenna arrangement is incorporated in the patient's table.

9. The computer tomograph according to claim 8, wherein the at least one of the first receiver antenna arrangement and the second transmitter antenna arrangement is incorporated in a berth of the patient's table.

10. The computer tomograph according to claim 3, wherein at least one antenna arrangement is embodied using non-metallic materials.

11. The computer tomograph according to claim 10, wherein at least one antenna arrangement is embodied using a non-metallic electrically conducting material.

12. The computer tomograph according to claim 11, wherein the non-metallic electrically conducting material comprises carbon.

13. The computer tomograph according to claim 3, wherein at least one antenna arrangement comprises dielectric waveguides.

14. The computer tomograph according to claim 9, wherein at least one antenna arrangement in the patient's table has an antenna pattern with a major lobe directed towards the rotating part.

15. The computer tomograph according to claim 14, wherein the major lobe is directed onto a plane perpendicular to the rotation axis of the rotating part.

16. The computer tomograph according to claim 9, wherein the control unit is configured to drive at least one antenna arrangement in the patient's table so that a major lobe of an antenna pattern of the at least one antenna arrangement is directed onto a plane of the rotating part, irrespective of shifts of the patient's table along a longitudinal direction.

17. The computer tomograph according to claim 9, wherein at least one antenna arrangement in the patient's table comprises a plurality of elements which extend in a transverse direction to the patient's table, and which are disposed along a longitudinal direction of the patient's table, wherein the control unit is configured to selectively employ one of the elements according to a position of the patient's table.

18. The computer tomograph according to claim 9, wherein at least one antenna arrangement in the patient's table comprises a plurality of elements which extend in a transverse direction to the patient's table, and which are disposed along a longitudinal direction of the patient's table, wherein the control unit is configured to drive phases which are shifted with respect to each other according to a position of the patient's table.

19. The computer tomograph according to claim 9, wherein the control unit is configured to control an antenna pattern of at least one antenna arrangement in the patient's table according to a rotational movement of the rotating part with respect to the stationary part.

20. The computer tomograph according to claim 3, wherein at least one antenna arrangement on the rotating part has an antenna pattern with a major lobe directed onto the patient's table.

21. The computer tomograph according to claim 3, wherein the control unit is configured to drive at least one antenna arrangement on the rotating part so that one major lobe of an antenna pattern of the at least one antenna arrangement is exactly directed onto a predetermined axis parallel to a rotation axis of the computer tomograph.

22. The computer tomograph according to claim 3, wherein the control unit is configured to drive at least one antenna arrangement on the rotating part so that one major lobe of an antenna pattern of the at least one antenna arrangement is exactly directed onto a predetermined position of the patient's table.

23. The computer tomograph according to claim 22, wherein the predetermined position is on the underside of the patient's table.

24. The computer tomograph according to claim 3, wherein the control unit is configured to feed a plurality of antennas of at least one antenna arrangement at a same phase referred to a reference signal.

25. The computer tomograph according to claim 3, wherein a plurality of antennas of at least one antenna arrangement are adapted for feeding a receiver unit at a same phase referred to a reference signal.

26. The computer tomograph according to claim 1, wherein the control unit is configured to provide bidirectional communication between the rotating part and the stationary part, the control unit pre-setting a time frame for communication in each of two directions.

27. A computer tomograph comprising a rotating part and a stationary part, with a system for transmission of data between the rotating part and the stationary part, in which the rotating part comprises:
    at least one data source;
    at least one first transmitter means for receiving data from the data source and converting received data to data signals for transmission to the stationary part; and
    a first transmitter antenna arrangement for transmitting the data signals;
wherein the stationary part comprises:
    a first receiver antenna arrangement for picking-up data signals transmitted by the first transmitter antenna arrangement;

at least one first receiver means for receiving data signals from the first receiver antenna arrangement and converting the received data signals for relay of data to a data sink;

at least one data sink for evaluating data relayed from the receiver means; and a patient's table adapted to move along a direction of an axis of the rotating part, wherein the first receiver antenna arrangement is incorporated in the patient's table.

28. The computer tomograph of claim 27, wherein the first receiver antenna arrangement is incorporated in a berth of the patient's table.

29. The computer tomograph of claim 27, wherein first receiver antenna arrangement comprises an antenna pattern with a major lobe directed towards the rotating part.

* * * * *